(12) United States Patent
Kimura et al.

(10) Patent No.: US 6,618,615 B1
(45) Date of Patent: Sep. 9, 2003

(54) APPARATUS FOR AND METHOD OF MEASURING BODY FAT

(75) Inventors: Eiichi Kimura, Osaka (JP); Emi Ashibe, Kyoto (JP); Naoki Yanai, Osaka (JP); Motonobu Shiomi, Osaka (JP); Nobuyoshi Yasuda, Osaka (JP)

(73) Assignees: Kurabo Industries Ltd., Okayama (JP); Arkray, Inc., Kyoto (JP)

( * ) Notice: Subject to any disclaimer, the term of this patent is extended or adjusted under 35 U.S.C. 154(b) by 0 days.

(21) Appl. No.: 09/621,585

(22) Filed: Jul. 21, 2000

(30) Foreign Application Priority Data

Jul. 23, 1999 (JP) .......................................... 11-209921
Mar. 6, 2000 (JP) ...................................... 2000-060088

(51) Int. Cl.[7] ................................................ A61B 5/00
(52) U.S. Cl. ..................................................... 600/473
(58) Field of Search ................................ 600/300, 310, 600/311, 473, 476; 356/432, 433

(56) References Cited

U.S. PATENT DOCUMENTS 5,086,229 A * 2/1992 Rosenthal et al. ..... 250/339.12
5,774,213 A * 6/1998 Trebino et al. ............. 356/320
6,134,458 A * 10/2000 Rosenthal ................... 600/310
6,336,044 B1 * 1/2002 Ghiassi et al. .............. 600/473
6,354,996 B1 * 3/2002 Drinan et al. ............... 600/300
6,405,065 B1 * 6/2002 Malin et al. ................ 600/310

* cited by examiner

Primary Examiner—Ruth S. Smith
(74) Attorney, Agent, or Firm—Rader, Fishman & Grauer PLLC

(57) ABSTRACT

A photometer comprises a projecting mechanism irradiating a physical mass with infrared light within a wavelength region of 1.1 to 2.0 $\mu$m, a photoreceiving mechanism receiving output light from the physical mass and a spectroscope separating the light applied to the physical mass or the output light from the physical mass into its spectral components, for measuring absorbance by the physical mass at a specific wavelength. A compression mechanism can compress a measured region of the physical mass or a peripheral portion thereof, and difference absorbance calculator obtains difference absorbance from first absorbance obtained by the photometer under a state compressed by the compression mechanism with a first pressure and second absorbance obtained by the photometer under a state compressed with a second pressure lower than the first pressure or a non-compressed state. A storage part stores a relation between body fat and difference absorbance, and an operation part quantitatively determines and outputs body fat from the difference absorbance calculated by the difference absorbance calculator on the basis of the relation stored in the storage part.

13 Claims, 7 Drawing Sheets

APPARATUS FOR AND METHOD OF MEASURING BODY FAT

BACKGROUND OF THE INVENTION

1. Field of the Invention

The present invention relates to an apparatus for quantitatively determining body fat of a physical mass including a human body, an animal body or a fish body, and a method of quantitatively determining body fat of a physical mass other than a human body, and more particularly, it relates to an apparatus for and a method of non-invasively quantitatively measuring body fat with infrared light

2. Description of the Prior Art

In relation to methods of non-invasively measuring body fat, apparatuses for irradiating organisms with light of visible to near-infrared regions of 600 to 1100 nm and quantitatively determining body fat on the basis of absorbance by the body fat are proposed (refer to National Patent Publication Gazette No. 4-500762 (1992) and Japanese Patent Laying-Open Gazette No. 10-94523 (1998)).

In one of such methods, visible light having a central wavelength in the range of 660 to 740 nm is employed. The reason for this is that a light source is formed by a light emitting diode or the like having a large half-band width. The wavelength region is superior for maintaining or improving measurement accuracy since absorbance-change-per-unit-wavelength is flat. Consequently, since a low-priced light emitting diode can be obtained, it is assumed that the light emitting diode can be implemented at a low cost while maintaining high accuracy Considering a physical mass including a human body, an animal body or a fish body, however, tissue components such as hemoglobin and melamine forming the physical mass have large absorption coefficients while the absorption coefficient of fat is small in this wavelength region.

Furthermore, the compositions of the tissue components subtly vary with measured regions or measuring persons, and hence the difference between the tissue components such as hemoglobin and melamine having large absorption coefficients exerts remarkable influence on the result of determination of the fat rate. In fact, it has been proven through measurements made by the inventors that no excellent correlation is obtained between a pannicular thickness and absorbance, and determination is difficult, not in the wavelength region, but even in a wavelength region exhibiting a larger absorption coefficient of fat (refer to FIG. 7 and description thereof made below).

SUMMARY OF THE INVENTION

The present invention is directed to a body fat measuring apparatus for measuring body fat of a physical mass including a human body, an animal body or a fish body, and a body fat measuring method of measuring body fat of a physical mass other than a human body, and an objective thereof is to improve quantitative determination accuracy for body fat.

The inventors have made measurements in a wavelength region exhibiting a large absorption coefficient by fat while varying a pressure for compressing a measured region or a peripheral portion thereof in two stages for obtaining the difference (difference absorbance) between absorbance values under the two compressed states, to find that there is correlation between the body fat and the difference absorbance.

FIG. 1 schematically expresses the present invention. A photometer 2 includes a projecting mechanism irradiating a physical mass with infrared light included in a wavelength region of 1.1 to 2.0 $\mu$m, a photoreceiving mechanism receiving output light from the physical mass through the light and spectroscopic means separating the light applied to the physical mass or the output light from the physical mass into its spectral components, for measuring absorbance by the physical mass at a specific wavelength. A compression mechanism 4 can compress a measured region of the physical mass or a peripheral portion thereof, and difference absorbance calculator 6 obtains difference absorbance from first absorbance obtained by the photometer 2 under a state compressed by the compression mechanism 4 with a first pressure and second absorbance obtained by the photometer 2 under a state compressed with a second pressure lower than the first pressure or a non-compressed state. A storage part 8 stores relation between body fat and difference absorbance, and an operation part 10 determines quantitatively and outputs body fat from the difference absorbance calculated by the difference absorbance calculator 6 on the basis of the relation stored in the storage part 8.

The relation between body fat and difference absorbance is, for example, a relational equation showing correlation obtained from body fat measured by known means and the difference absorbance measured by the inventive apparatus and the storage part 8 stores such a relational equation for quantitative determination.

The term body fat includes a fat thickness and a fat rate.

A body fat measuring method according to the present invention is a method of quantitatively measuring body fat of a physical mass by carrying out a photometric step of irradiating a physical mass other than a human body with infrared light included in a wavelength region of 1.1 to 2.0 $\mu$and receiving output light from the physical mass through the light for measuring absorbance by the physical mass at a specific wavelength under two states, i.e., a state compressed with a first pressure and a state compressed with a second pressure lower than the first pressure or a non-compressed state, obtaining difference absorbance from the difference between the absorbance values obtained under the respective states and quantitatively determining body fat on the basis of the difference absorbance.

In the wavelength region of 1.1 to 2.0 $\mu$m, absorption coefficients of hemoglobin and melamine reduce and the absorption coefficient of fat increases. Therefore, measurement in this wavelength region is advantageous for quantitative determination of fat. While light absorption by tissue components other than fat is still present in the wavelength region of 1.1 to 2.0 $\mu$m, fat can be quantitatively determined on the basis of difference absorbance by making measurement while varying the pressure for compressing the measured region or the peripheral portion thereof in two ages and obtaining the difference absorbance.

Thus, determination accuracy for fat is improved due to selection of the wavelength region exhibiting a large absorption coefficient of fat and difference absorbance obtained under two stages of compressed states.

The term "compressed state" on a lower pressure side means not only compression under a low pressure but also a non-compressed state.

A body fat measuring apparatus according to the present invention is firstly directed to a human body. A pannicular thickness or a fat rate can be measured and utilized for health care or the like.

The body fat measuring apparatus according to the present invention is secondly directed to a physical mass other than a human body, i.e., the body of animals such as cows, pigs and whales, and/or fish such as tuna and yellowtail. The pannicular thickness or the fatty rate of such a live physical mass can be percutaneously measured for evaluating the quality as edible meat The apparatus is also applicable to percutaneous measurement in a carcass or dissociated state.

The body fat measuring method according to the present invention is directed to a physical mass other than a human body. This measuring method can be executed not only with the aforementioned measuring apparatus according to the present invention but also with another measuring apparatus.

FIG. 2 shows an absorption spectrum of beef tallow. In this spectrum, peaks "a" and "c" are by fat and a peak "b" is by water. The peak top wavelength of the peak "a" is around 1.21 μm (8264 cm$^{-1}$), and the peak top wavelength of the peak "c" is around 1.72 μm (5814 cm$^{-1}$). Therefore, a wavelength around 1.21 μm or 1.72 μm is preferably selected for measuring absorbance of fat.

When performing two-wavelength measurement, two wavelengths of a first wavelength (measuring wavelength) around 1.21 μm or 1.72 μm and a second wavelength (reference wavelength) exhibiting a small absorption coefficient of body fat are selected as wavelengths for measuring absorbance, and difference absorbance is obtained. Absorbance under each compressed state is preferably obtained by subtracting absorbance at the reference wavelength from absorbance at the measuring wavelength.

The reason for employing the difference between the absorbance at the measuring wavelength and the absorbance at the reference wavelength is as follows: In general, fluctuation of a baseline takes place in a spectrum. A temperature drift of an apparatus, ambient temperature change, deterioration of a light source, sensitivity change or deterioration of a detector caused by a temperature, change of a scattered state of a measured object, the degree of contact between the measured object and a measuring probe, reproducibility of the position of a measured region and the like can be listed as the causes. Therefore, when employing the difference between the absorbance at the measuring wavelength and the absorbance at the reference wavelength, these fluctuation factors are eliminated and absorbance can be measured with excellent reproducibility.

However, the present invention is not restricted to cases of employing the absorbance difference but also applicable to cases of obtaining difference absorbance under different compressed states on the basis of absorbance at the measuring wavelength.

The first pressure applied by the compression mechanism 4 is preferably set to 1.0 to 3.0 kPa, and the second pressure is preferably set to less than 1.0 kPa. If the measured object is not a human body, the first pressure may be further increased. However, if the measured object is a human body, the first pressure is preferably not excessively increased to prevent pain.

According to the present invention, correlation with body fat is improved and quantitative determination accuracy for body fat is increased by employing the wavelength region of 1.1 to 2.0 μm having a large absorption coefficient of fat, making measurements while varying the pressure for compressing the measured region or the peripheral portion thereof in two stages and obtaining the difference between the absorbance values under the two compressed states.

When measuring body fat of a human body with the inventive measuring apparatus, quantitative data useful for health care can be provided.

When applying the measuring apparatus and the measuring method according to the present invention to a physical mass other than a human body, body fat of an animal or fish for edible meat can be measured in a live. state for controlling the quality of the meat The body fat of a physical mass other than a human body must be measured also in a carcass state before and after dissociation. Therefore, the measuring apparatus and the measuring method according to the present invention can provide quantitative data useful for quality control of a physical mass other than a human body.

The foregoing and other objects, features, aspects and advantages of the present invention will become more apparent from the following detailed description of the present invention when taken in conjunction with the accompanying drawing.

DESCRIPTION OF THE PREFERRED EMBODIMENTS

Figure 3:
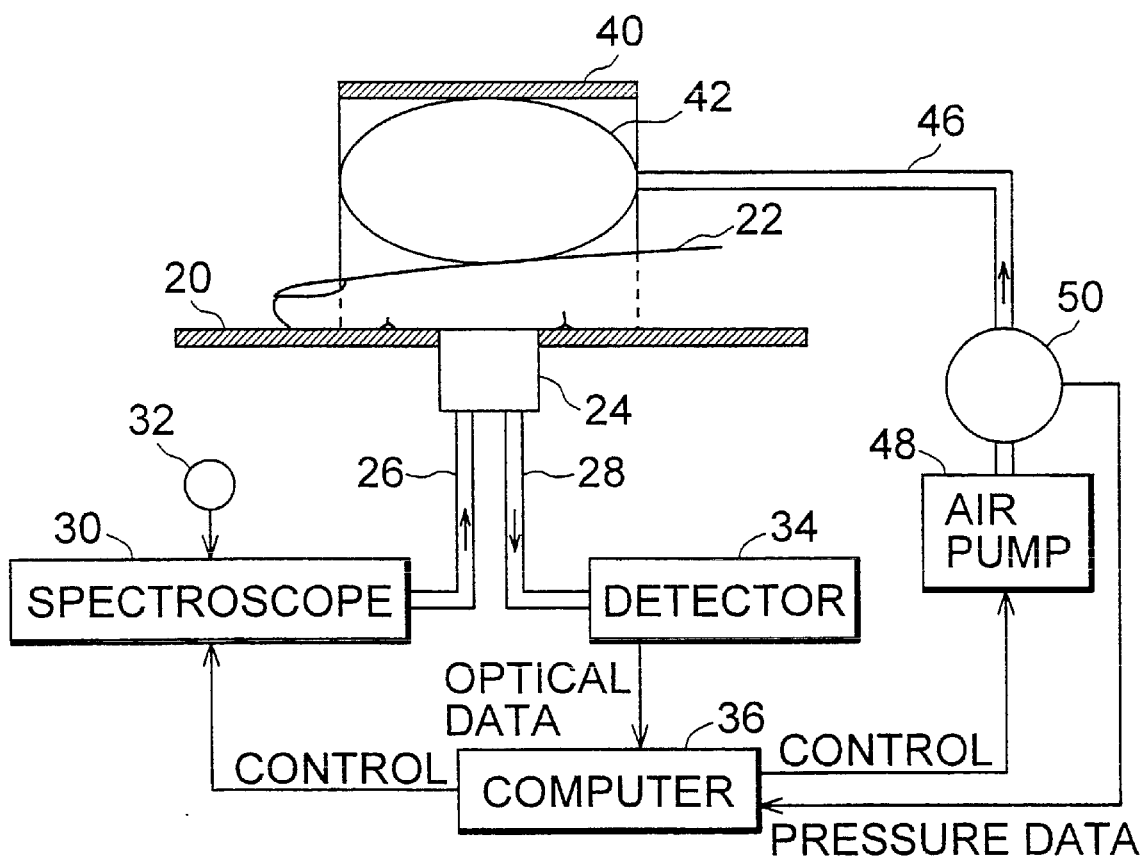
FIG. 3 is a schematic block diagram showing an embodiment of the present invention.

FIG. 3 shows an embodiment of the present invention. While the embodiment is on the assumption that a measured object is a human body, the present invention also includes those applied to other measured objects.

A finger, which is a measured object 22, is placed on a table 20 while directing its cushion toward the table 20. A probe 24 is engaged in the table 20 so that the forward ends of optical fiber bundles 26 and 28 are fixed to the probe 24 and the forward end surfaces thereof are exposed from the probe 24 to come into contact with the measured object 22 placed on the table 20.

The base end of the optical fiber bundle 26 is connected to a spectroscope 30, which in turn separates light from a light source 32 into its spectral components and guides the same to the optical fiber bundle 26. The measured object 22 is irradiated with infrared light for measurement from the forward end surface of the optical fiber bundle 26. The light source 32, emitting infrared light included in a wavelength region of 1.1 to 2.0 μm, may include a continuous spectrum of this wavelength region or discontinuous bright line spectra. The light source 32 can be prepared from an LED (light-emitting diode) or an LD (laser diode) for emitting infrared light, in addition to a tungsten-halogen lamp. The probe 24, the optical fiber bundle 26 and the light source 32 form an exemplary projecting mechanism.

Scattered light of the infrared light applied to and entering the measured object 22 is incident upon the forward end surface of the optical fiber bundle 28. The base end of the optical fiber bundle 28 is connected to a detector 34, which in turn detects the intensity of the light guided by the optical fiber bundle 28 and transmits the same to a computer 36 as optical data. The detector 34, sensitive to the wavelength of the infrared light applied to the measured object 22, can be formed by a Ge photodiode, an InGaAs photodiode, a PbS photoconductive element, a PbSe photoconductive element, an InAs photovoltaic element, a pyroelectric element or the like. The probe 24, the optical fiber bundle 28 and the detector 34 form an exemplary photoreceiving mechanism.

The spectroscope 30 is controlled by the computer 36 to be capable of scanning the wavelength and measuring a spectrum. While the spectroscope 30 is arranged in a position for separating the light not yet applied to the measured object 22 into its spectral components to take a pre-spectroscopic system in this embodiment, the spectroscope 30 may alternatively be arranged on a position for separating the light scattered through the measured object 22 into its spectral components to take a post-spectroscopic system.

The probe 24, the optical fiber bundles 26 and 28, the spectroscope 30, the light source 32, the detector 34 and the computer 36 form the photometer 2, to be capable of measuring absorbance by a human body at a specific wavelength.

A housing 40 is mounted on the table 20 in a region including the probe 24 in order to compress the measured object 22 placed on the table 20, and an air pack 42 is arranged for compressing the measured object 22 set in the housing 40. An air pump 48 feeds air to the air pack 42 through an air pipe 46, so that the air pack 42 can compress the measured object 22. The air pipe 46 is provided with a pressure gauge 50 for measuring the compression pressure of the air pack 42. The computer 36 captures the pressure measured by the pressure gauge 50 and controls the air pump 48 so that the pressure reaches a prescribed value. Thus, the measured object 22 is compressed with a prescribed pressure through the air pack 42. The housing 40, the air pack 42, the air pipe 46, the air pump 48, the pressure gauge 50 and the computer 36 form an example of the compression mechanism 4.

Figure 1:
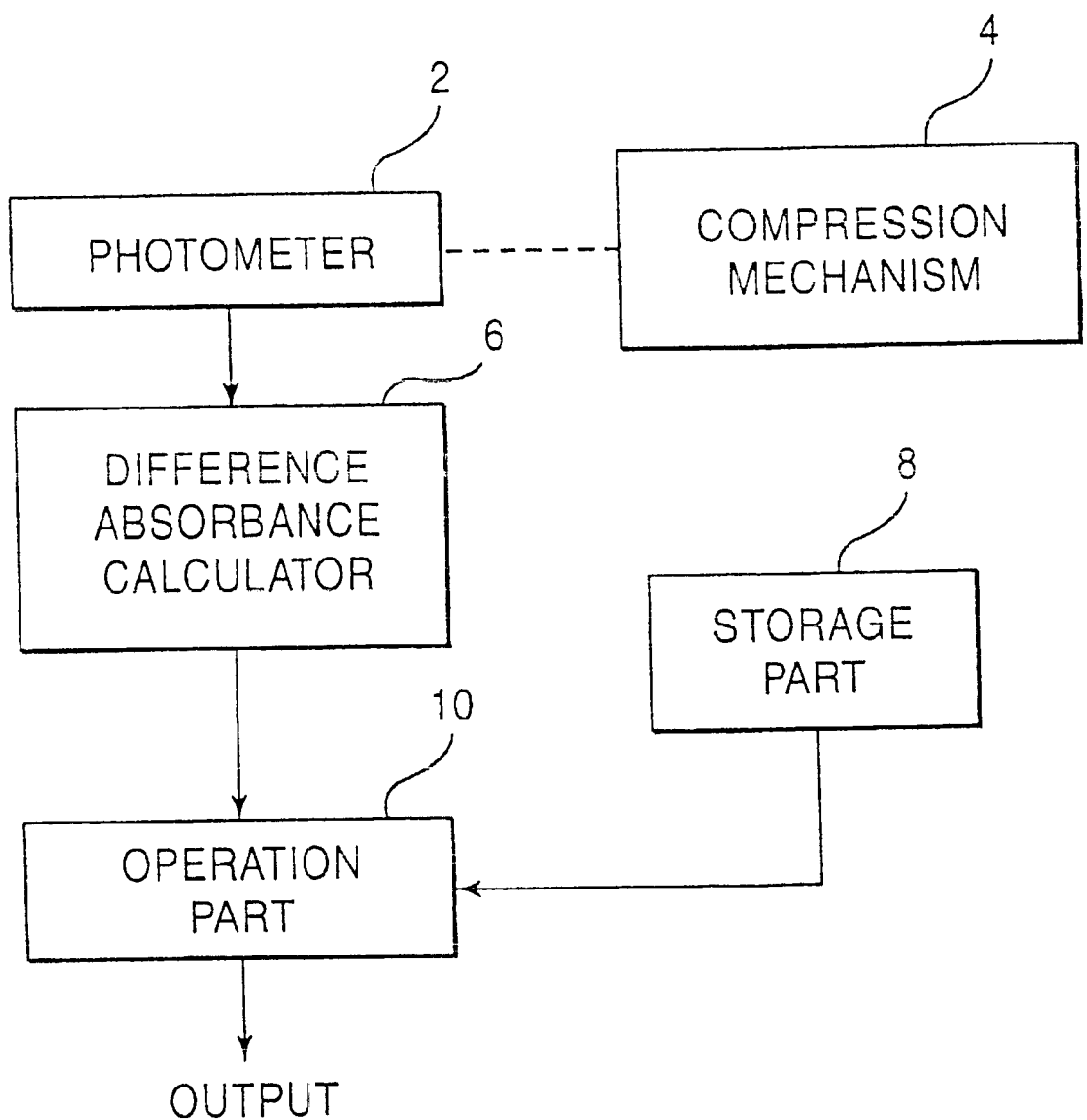
FIG. 1 is a block diagram schematically showing the present invention.
Figure 2:
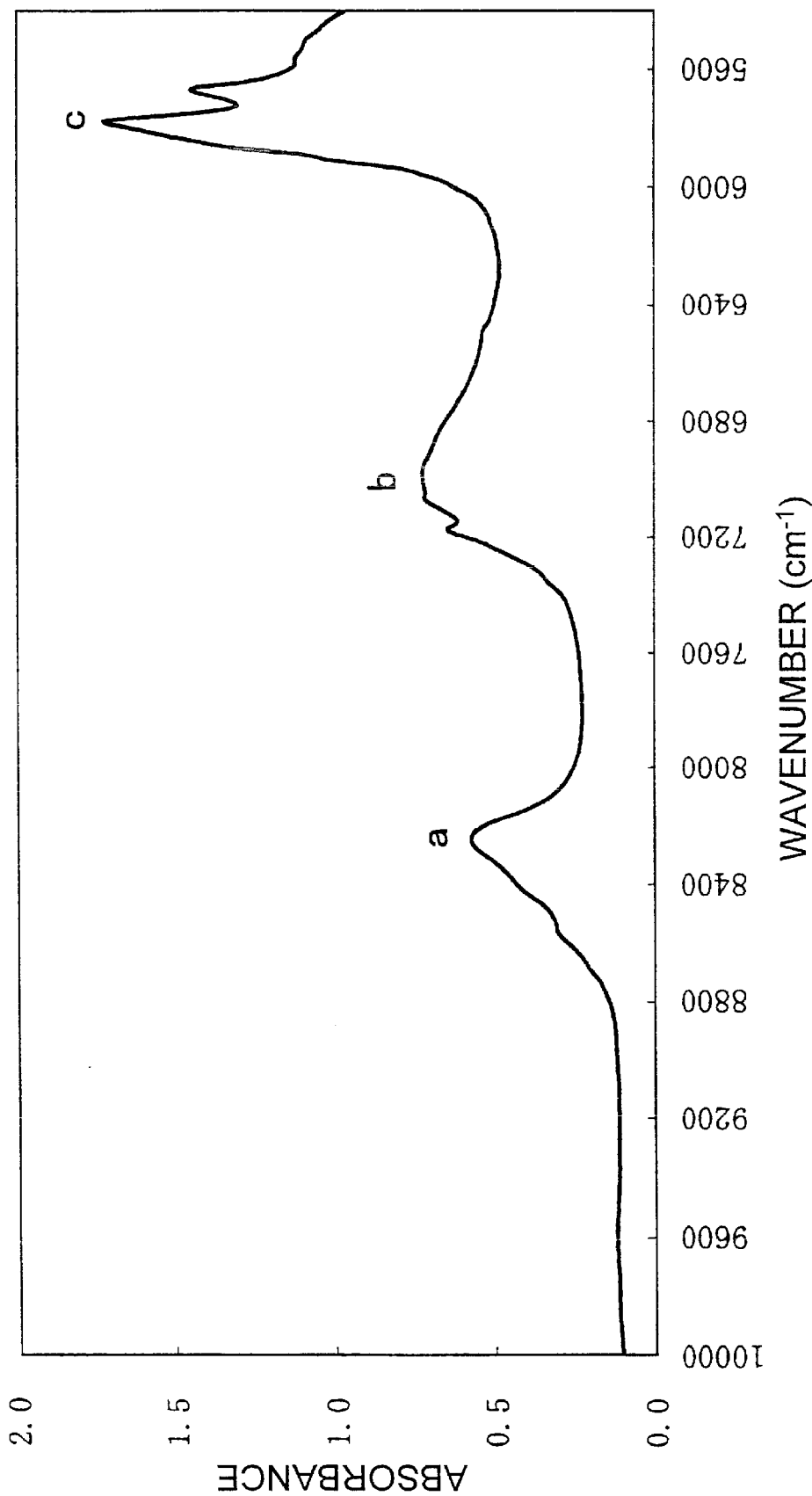
FIG. 2 is a waveform diagram showing an absorption spectrum of beef tallow.

The computer 36 implements the functions of the difference absorbance calculator 6, the storage part 8 and the operation part 10 shown in FIG. 1. However, the difference absorbance calculator 6 may be implemented not by a computer but by an electric circuit through combination of a logarithmic amplifier and a subtracter.

In this embodiment, the finger being the measured object 22 is placed on the table 20 as shown in FIG. 3, and the air pump 48 supplies air to the air pack 42 by an instruction from the computer 36 for compressing the finger of the measured object 22 with a prescribed pressure of, for example, 0.2 kPa. In this state, the spectroscope 30 separates the infrared light from the light source 32 into its spectral components, and applies the same to the measured object 22 through the optical fiber bundle 26. The infrared light applied to the measured object 22 is scattered through the measured object 22 and thereafter incident upon the optical fiber bundle 28, to be guided to and detected by the detector 34. The spectroscope 30 scans the wavelength of the infrared light applied to the measured object 22, thereby obtaining a scattered light spectrum under the compressed state.

Next, the air pump 48 further supplies air to the air pack 42 by an instruction from the computer 36 for compressing the measured object 22 with a prescribed pressure of, for example, 3.0 kPa higher than the aforementioned pressure and similarly obtaining a scattered light spectrum under the compressed state.

Figure 4:
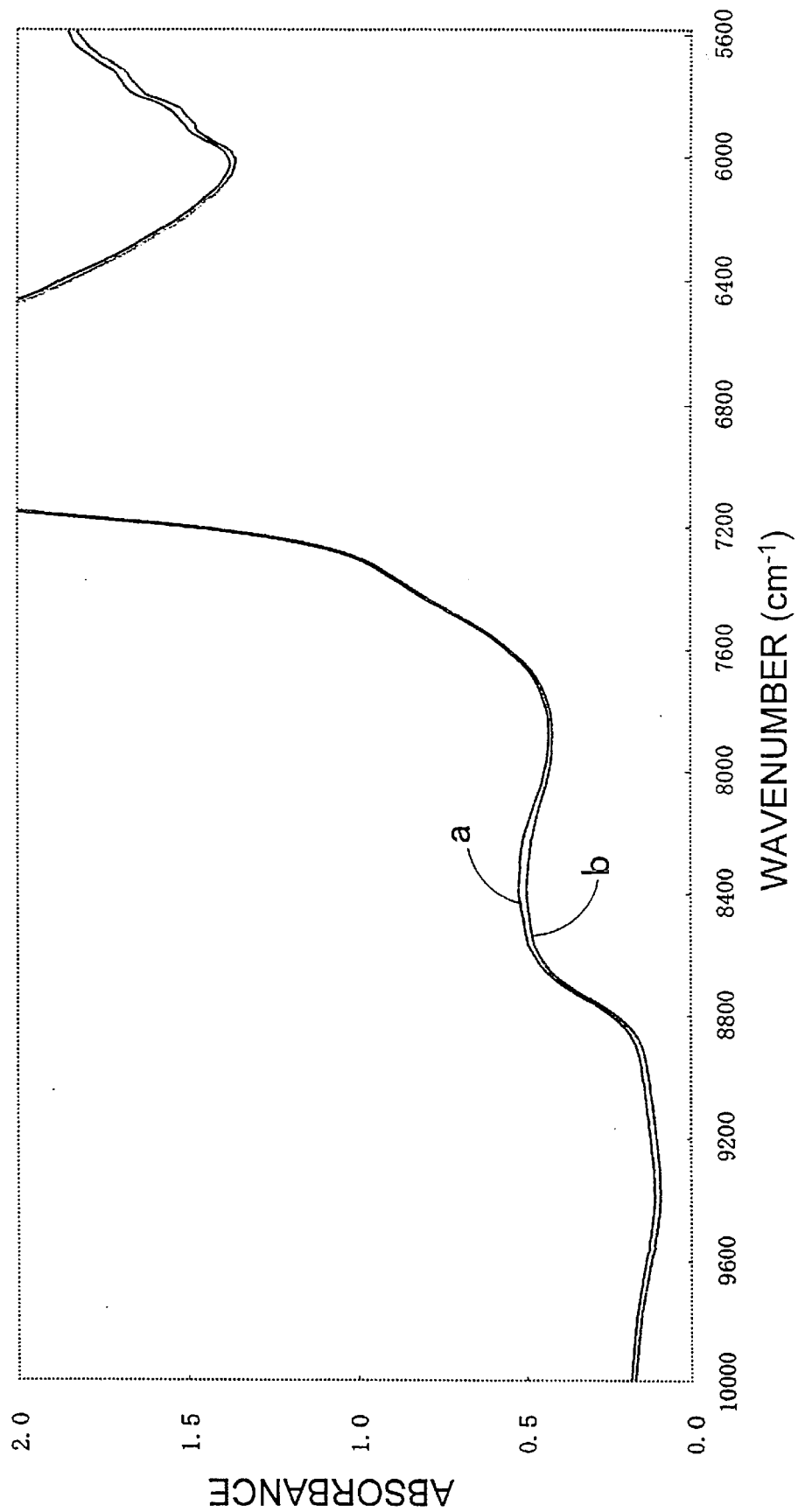
FIG. 4 is a waveform diagram showing scattered light spectra under two compressed states measured in the embodiment.

FIG. 4 shows the scattered light spectra under the two compressed states. The spectrum (a) having large absorbance is obtained under the compressed state with the low pressure of 0.2 kPa, and the spectrum (b) having small absorption is obtained under the compressed state with the high pressure of 3.0 kPa.

Figure 5:
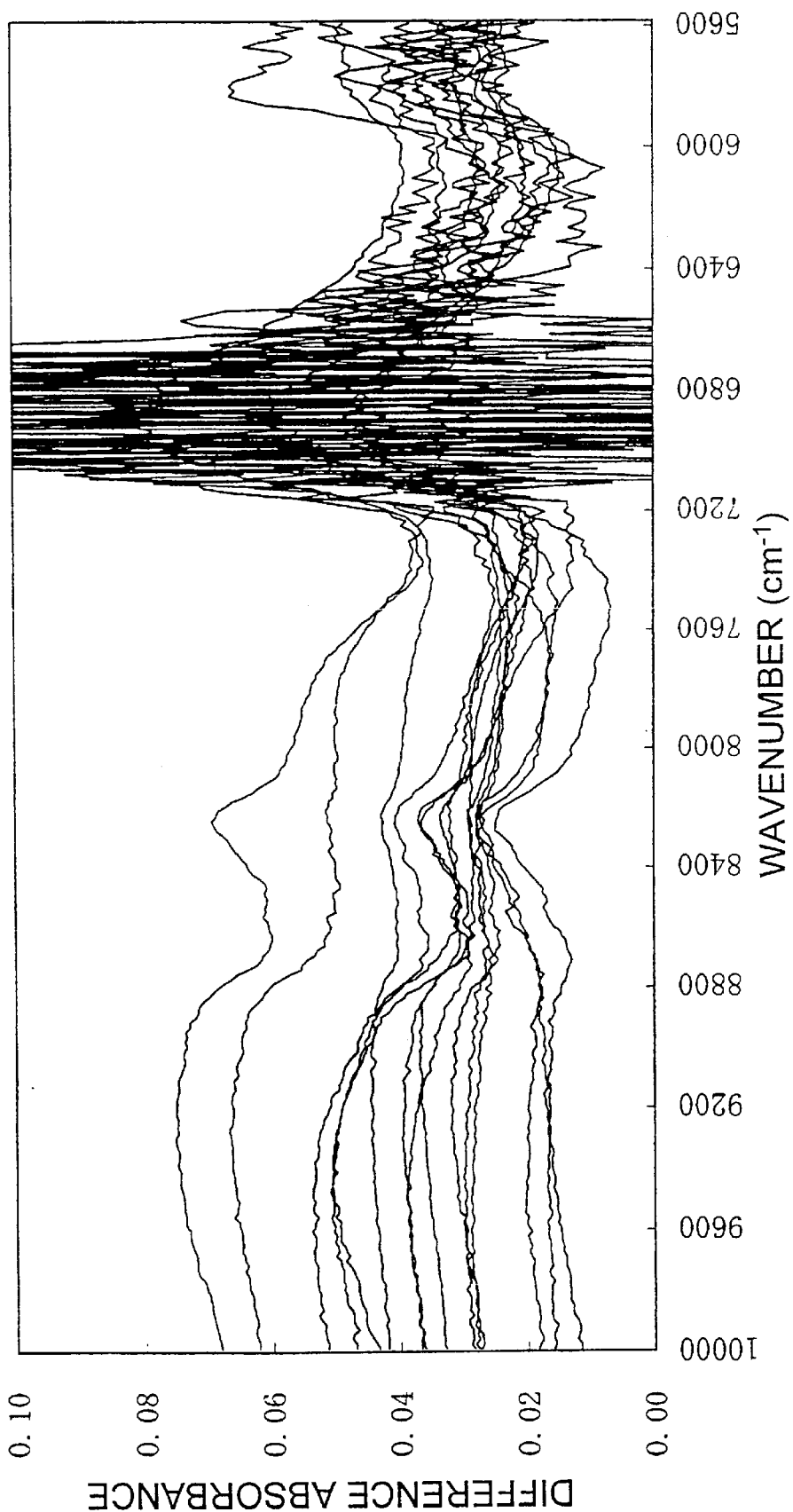
FIG. 5 is a waveform diagram showing difference absorbance spectra obtained by measuring scattered light spectra on various regions having different pannicular thicknesses in the embodiment.

A difference absorbance spectrum can be obtained by obtaining the difference between the scattered light spectra under the two compressed states. FIG. 5 shows difference absorbance spectra obtained by measuring scattered light spectra under two stages of compressed states as shown in FIG. 4 on various regions having different pannicular thicknesses as follows:

Difference Absorbance=(Absorbance at 3 kPa)−(Absorbance at 0.2 kPa)

Figure 6:
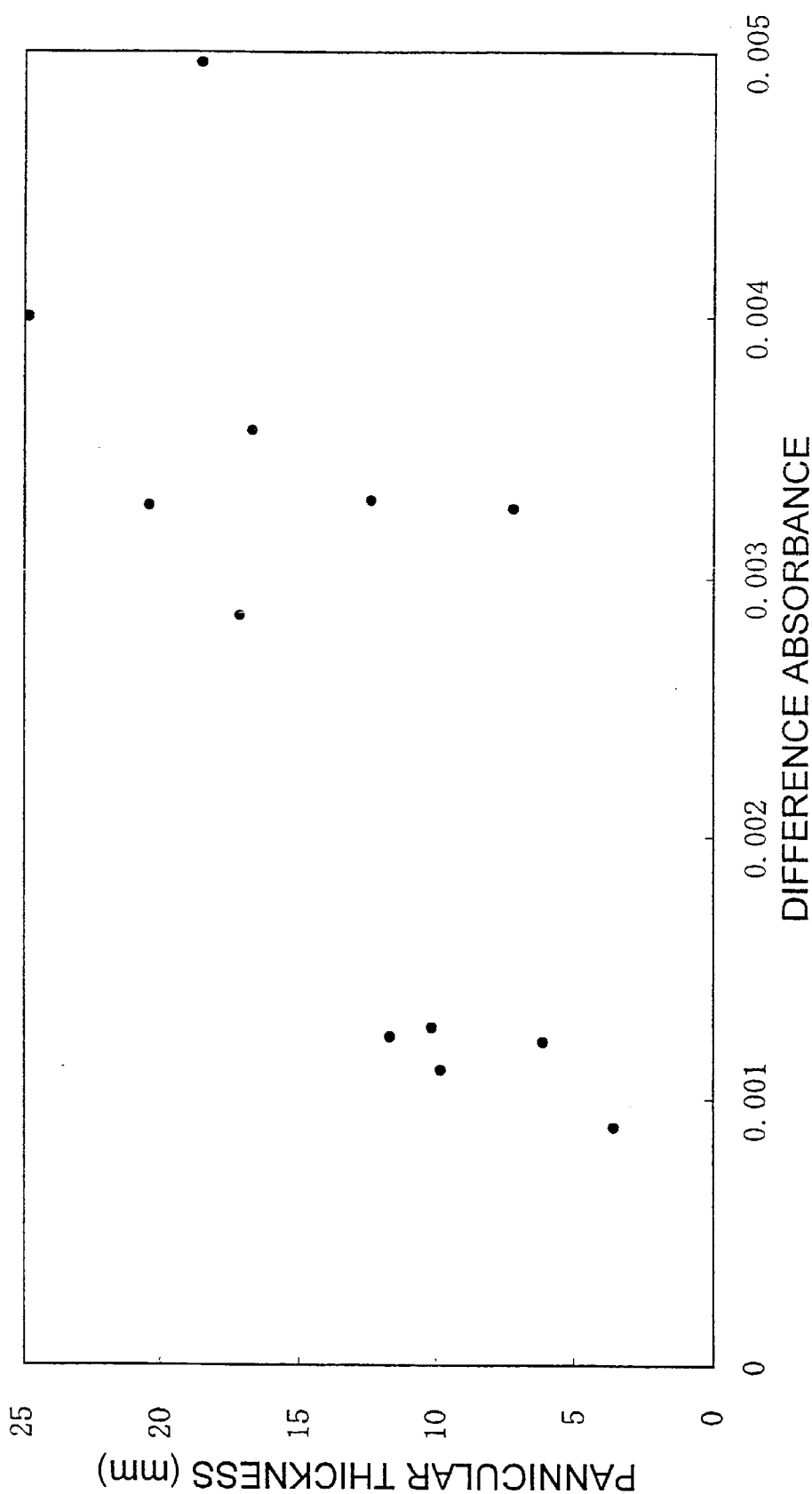
FIG. 6 is a waveform diagram showing correlation between the pannicular thicknesses and the difference absorbance values measured in the embodiment.

FIG. 6 shows correlation between the pannicular thicknesses and the difference absorbance values on the basis of the results shown in FIG. 5. The pannicular thicknesses were directly measured by holding the regions with calipers. The absorbance under each compressed state was obtained as absorbance difference by a two-wavelength method at 1.21 $\mu$m with reference to absorbance at 1.15 $\mu$m as follows:

Absorbance=(Absorbance at 1.21 $\mu$m)−(Absorbance at 1.15 $\mu$m)

It is understood from the results shown in FIG. 6 that there is correlation between the pannicular thicknesses and the difference absorbance values although dispersion of the measured values of the pannicular thicknesses is large. A relational expression indicating the correlation can be obtained from such results of measurement so that the storage part 8 stores the same for quantitative determination.

Figure 7:
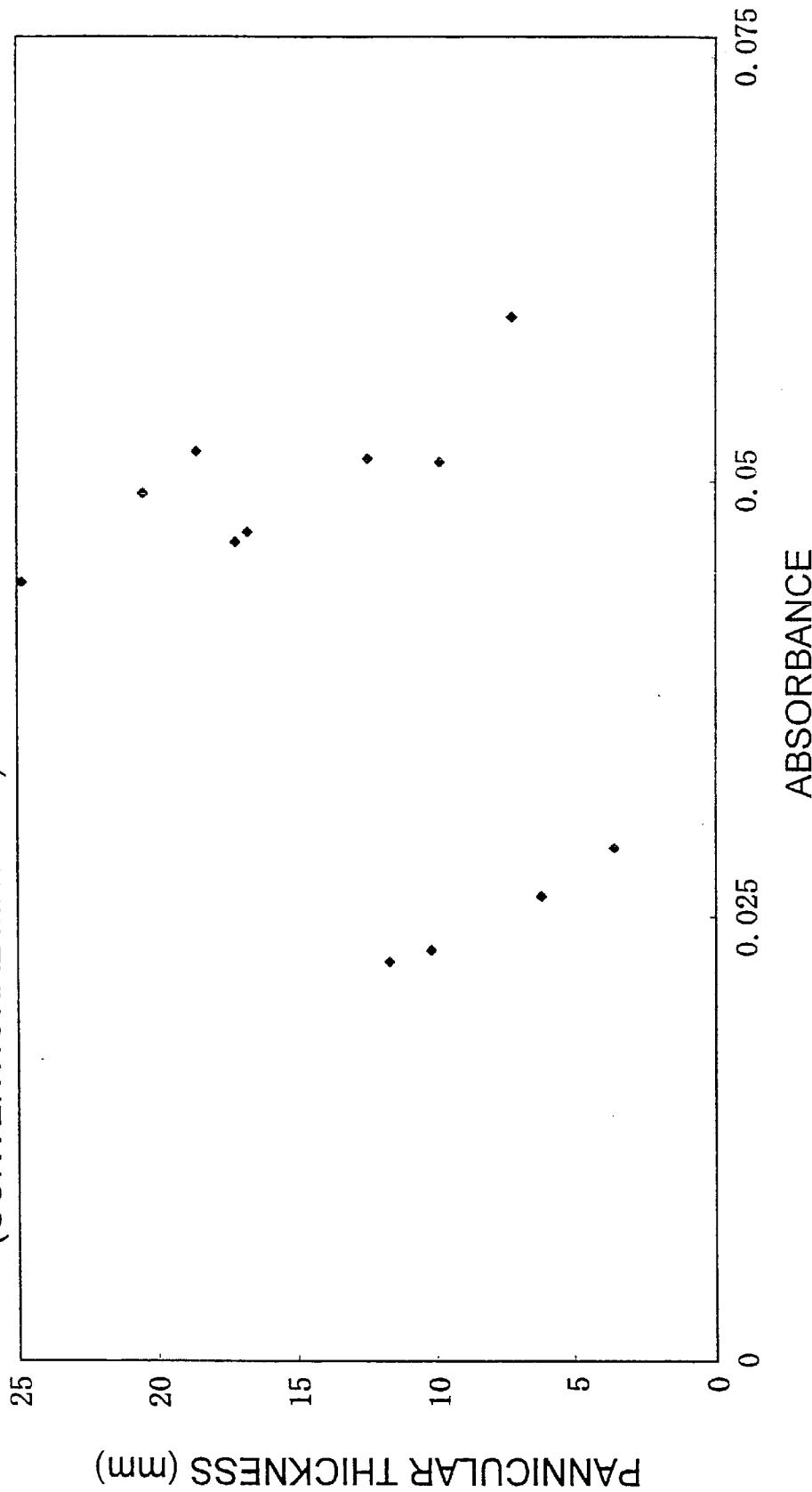
FIG. 7 is a waveform diagram showing correlation between absorbance values under a state compressed at 0.2 kPa and pannicular thicknesses.

For comparison with these results, correlation with pannicular thicknesses was obtained by employing absorbance under one compressed state with the pressure of 0.2 kPa. FIG. 7 shows the results. Similar results are obtained also when making measurement under a non-compressed state. It is understood that the correlation of the results shown in FIG. 7 is inferior to the correlation of the results shown in FIG. 6 and the correlation with the pannicular thicknesses is improved by obtaining the difference between the absorbance values under the two stages of compressed states according to the present invention.

Although the present invention has been described and illustrated in detail, it is clearly understood that the same is by way of illustration and example only and is not to be taken by way of limitation as the spirit and scope of the present invention are limited only by the terms of the appended claims.

What is claimed is:

1. A body fat measuring apparatus for measuring body fat of a physical mass including a human body, an animal body or a fish body, comprising:

a photometer for measuring absorbance by the physical mass at at least one wavelength including a projecting mechanism for irradiating the physical mass with infrared light included in a wavelength region of 1.1 to 2.0 $\mu$m, a photoreceiving mechanism for receiving output light from the physical mass and spectroscopic means for separating said light to be applied to the physical mass or said output light from the physical mass into its spectral components;

a compression mechanism for compressing a measured region of the physical mass or a peripheral portion thereof;

difference absorbance calculation means for obtaining difference absorbance from first absorbance obtained by said photometer under a first state in which the measured region is compressed by said compression mechanism with a first pressure and second absorbance obtained by said photometer under a second state in which the measured region is either compressed with a second pressure lower than said first pressure or non-compressed;

a storage part storing relations between body fat and difference absorbance; and an operation part quantitatively determining body fat from said difference absorbance calculated by said difference absorbance calculation means on the basis of said relations stored in said storage part.

2. The body fat measuring apparatus according to claim 1, wherein said first pressure is 1.0 to 3.0 kPa and said second pressure is less than 1.0 kPa.

3. The body fat measuring apparatus according to claim 1, wherein said wavelength for measuring absorbance is around 1.21 $\mu$m.

4. The body fat measuring apparatus according to claim 1, wherein said wavelength for measuring absorbance is around 1.72 $\mu$m.

5. The body fat measuring apparatus according to claim 1, wherein said at least one wavelength for measuring absorbance includes a first wavelength around 1.21 $\mu$m and a second wavelength having a small absorption coefficient of fat, and said absorbance under each said first and second states for obtaining said difference absorbance is obtained by subtracting absorbance at said second wavelength from absorbance at said first wavelength.

6. The body fat measuring apparatus according to claim 1, wherein said at least one wavelength for measuring absorbance includes a first wavelength around the 1.72 $\mu$m and a second wavelength having a small absorption coefficient of fat, and said absorbance under each said first and second states for obtaining said difference absorbance is obtained by subtracting absorbance at said second wavelength from absorbance at said first wavelength.

7. A body fat apparatus for measuring body fat of a finger of a human body, comprising:

a photometer for measuring absorbance by the finger at at least one wavelength including a projecting mechanism for irradiating the finger with infrared light included in a wavelength region of 1.1 to 2.0 $\mu$m, a photoreceiving mechanism for receiving output light from the finger and spectroscopic means for separating said light to be applied to the finger or said output light from the finger into its spectral components;

a compression mechanism for compressing a measured region of the finger or a peripheral portion thereof;

difference absorbance calculation means for obtaining difference absorbance from first absorbance obtained by said photometer under a first state in which the measured region is compressed by said compression mechanism with a first pressure and second absorbance obtained by said photometer under a second state in which the measured region is either compressed with a second pressure lower than said first pressure or non-compressed;

a storage part storing relations between body fat and difference absorbance; and an operation part quantitatively determining body fat from said difference absorbance calculated by said difference absorbance calculation means on the basis of said relations stored in said storage part, wherein said photometer includes a table for receiving the finger and a probe engaged in said table for brining a projecting end of said projecting mechanism and a photoreceiving end of said photoreceiving mechanism into contact with the finger on said table, and said compression mechanism includes an air pack compressing the finger placed on said table from a side opposite to said probe.

8. A body fat measuring method including:

(A) a first photometric step of irradiating a physical mass other than a human body with infrared light including a wavelength region of 1.1 to 2.0 $\mu$m under a first state in which the physical mass is compressed with a first pressure and receiving output light from the physical mass for measuring absorbance by the physical mass at at least one wavelength;

(B) a second photometric step of irradiating the physical mass with said infrared light under a second state in which the physical mass is either compressed with a second pressure lower than said first pressure or non-compressed and receiving output light from the physical mass through said light for measuring absorbance by said physical mass at said wavelength;

(C) a step of obtaining difference absorbance from difference between said absorbance obtained in said first photometric step and said absorbance obtained in said second photometric step; and (D) quantitatively measuring body fat on the basis of said difference absorbance.

9. The body fat measuring method according to claim 8, wherein said first pressure is 1.0 to 3.0 kPa and said second pressure is less than 1.0 kPa.

10. The body fat measuring method according to claim 8, wherein said wavelength for measuring absorbance is around 1.21 $\mu$m.

11. The body fat measuring method according to claim 8, wherein said wavelength for measuring absorbance is around 1.72 $\mu$m.

12. The body fat measuring method according to claim 8, wherein said at least one wavelength for measuring absorbance includes two wavelengths of a first wavelength around 1.21 $\mu$m and a second wavelength having a small absorption coefficient of fat, and said absorbance under each said first and second states for obtaining said difference absorbance is obtained by subtracting absorbance at said second wavelength from absorbance at said first wavelength.

13. The body fat measuring method according to claim 8, wherein said at least one wavelength for measuring absorbance includes a first wavelength around 1.72 $\mu$m and a second wavelength having a small absorption coefficient of fat, and said absorbance under each said first and second states for obtaining said difference absorbance is obtained by subtracting absorbance at said second wavelength from absorbance at said first wavelength.

* * * * *